United States Patent [19]

Shuster

[11] Patent Number: 5,674,706
[45] Date of Patent: Oct. 7, 1997

[54] HIGH LEVEL EXPRESSION OF PROTEINS IN YEAST

[75] Inventor: Jeffrey R. Shuster, Walnut Creek, Calif.

[73] Assignee: Chiron Corporation, Emeryville, Calif.

[21] Appl. No.: 441,226

[22] Filed: May 15, 1995

Related U.S. Application Data

[63] Continuation of Ser. No. 397,553, Mar. 1, 1995, which is a continuation of Ser. No. 957,630, Oct. 6, 1992, which is a continuation of Ser. No. 190,868, May 6, 1988, abandoned.

[51] Int. Cl.$^6$ .............................. C12P 21/02; C12N 1/15
[52] U.S. Cl. ................................... 435/69.1; 435/254.21
[58] Field of Search ............................... 435/69.1, 182.1, 435/183, 252.3, 320.1, 254.21

[56] References Cited

U.S. PATENT DOCUMENTS 4,880,734  11/1989  Burke et al. ..................... 435/69.1

OTHER PUBLICATIONS

Schultz et al., *Gene*, vol. 61, 1987, pp. 123–133.
Denis, *Mol. Gen. Genet.*, vol. 208, 1987, pp. 101–106.

*Primary Examiner*—James Ketter
*Attorney, Agent, or Firm*—Ling-Fong Chung; Robert P. Blackburn

[57] ABSTRACT

A method is provided for expressing non-yeast proteins under the control of ADH2 regulatory sequences in a yeast host having enhanced expression of ADR I. Transformed yeast hosts are also provided.

21 Claims, 3 Drawing Sheets

HIGH LEVEL EXPRESSION OF PROTEINS IN YEAST

This application is a continuation of application Ser. No. 08/397,553, filed 1 Mar. 1995, which is a continuation of application Ser. No. 07/957,630, filed 6 Oct. 1992, which is a continuation of application Serial No. 07/190,868, filed 6 May 1988, now abandoned.

TECHNICAL FIELD

The present invention is directed to methods and materials useful for the production of heterologous proteins in yeast by recombinant DNA methods. More particularly, the present invention is directed to methods and materials which improve the yield of heterologous proteins made in yeast when said yeast are expressed under the control of a yeast alcohol dehydrogenase isoenzyme II (ADH II) gene promoter or its upstream activation sequence (UAS).

BACKGROUND

The expression of foreign genes in yeast regulated by the system which causes the expression of ADH II has proved to be quite valuable. Such expression usually involves placing the sequence encoding the heterologous protein under the control of the promoter from the ADH2 gene, or hybrid promoters employing the upstream regulatory region of the ADH2 promoter in combination with a strong yeast promoter, such as the glyceraldehyde-3-phosphate (GAP) promoter. See, e.g., EPO Pub. No. 164,556; EPO Pub. No. 196,056; commonly owned U.S. patent application Ser. No. 868,639, filed 29 May 1986. Expression cassettes for the heterologous protein employing the ADH2 regulatory regions are usually present in the yeast expression host in high copy numbers. While good results are obtained with such expression systems, a continuing need exists to enhance heterologous protein yield.

A number of studies have been published regarding regulation of the ADH2 gene by the yeast ADR1 gene. See, e.g., Shuster et al. (1986) Mol. Cell. Biol. 6:1894–1902; Denis et al. (1983) Mol. Cell. Biol. 3:360–370. Several studies have been published examining the relationship between the expression level of ADR1 and the expression level of native ADH2 genes. See Irani et al. (1987) Mol. Cell. Biol. 7:1233–1241; Denis (1987) Mol. Genet. 208:101–106. These studies however, did not demonstrate whether increased ADR1 expression would ultimately improve the yield of a heterologous protein expressed under the control of ADH2 regulatory sequences. For example, it was observed by Irani et al. (1987) that over one hundred copies of ADR1 did not overcome the 3- to 4-fold inhibition in ADH2 transcription caused by multiple ADH2 promoters. It was suggested that this result supports a model of ADH II regulation in which there are positive limiting factors, on ADH2 expression other than ADR1. Denis (1987) also reported that increasing ADR1 gene dosage was apparently toxic to the yeast host, resulting in a significant increase in cell doubling time.

SUMMARY OF THE INVENTION

It has been surprisingly discovered that the yield of heterologous protein by a yeast host transformed with an expression cassette for the heterologous protein employing the ADH2 regulatory system can be significantly enhanced by increasing the expression in the yeast host of the protein encoded by the ADR1 gene. This result is surprising in view of the reported toxicity of increased ADR1 gene dosage and the minimal effect of 100+ copies of the ADR1 gene on ADH II activity in a yeast host transformed with multiple ADH2 promoters.

In one embodiment, the present invention is directed to a method of expressing a heterologous protein in yeast comprising: providing a yeast host transformed by: (i) an expression cassette for said non-yeast protein comprising a DNA coding sequence for said non-yeast protein under the control of yeast-recognized transcription initiation and termination sequences functional in said yeast host, said transcription initiation sequence further comprising a yeast ADH2 upstream activation site; and (ii) an expression cassette for yeast ADR I comprising a DNA coding sequence for said ADR I under the control of yeast-recognized transcription initiation and termination sequences functional in said yeast host; (b) culturing a clonal population of said transformed yeast host under conditions whereby said non-yeast protein and said ADR I are expressed; and (c) recovering said non-yeast protein from said clonal population.

In another embodiment, the present invention is directed to a yeast cell transformed by: (a) an expression cassette comprising a DNA coding sequence for a non-yeast protein under the control of yeast-recognized transcription initiation and termination sequences functional in said yeast host, said transcription initiation sequence comprising a yeast ADH2 upstream activation site; and (b) an expression cassette for ADR I comprising a DNA coding sequence for said ADR I under the control of yeast-recognized transcription initiation and termination sequences functional in said yeast host.

In yet another embodiment, the present invention comprises a transformed yeast comprising an expression cassette integrated into the genome containing a coding sequence for ADR I under the control of yeast-recognized transcription initiation and termination sequences, said transcription initiation sequence being other than the ADR1 promoter.

These and other embodiments of the present invention will be readily apparent to those of ordinary skill in the art from the following description.

DETAILED DESCRIPTION

Figure 1:
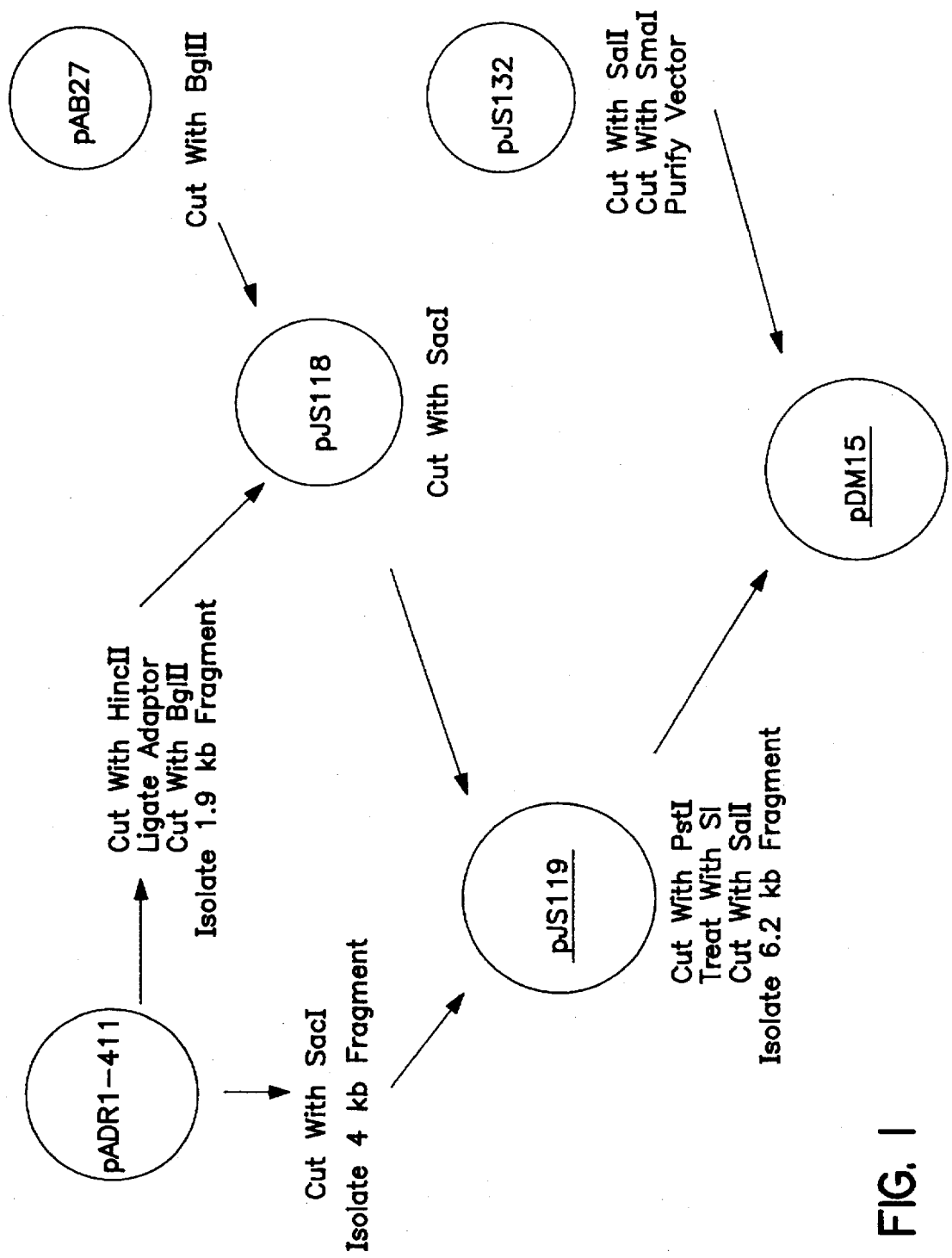
FIG. 1 is a flow diagram showing the construction of plasmids pJS119 and pDM15.

The practice of the present invention will employ, unless otherwise indicated, conventional molecular biology, microbiology, and recombinant DNA techniques within the skill of the art. Such techniques are fully explained in the literature. See, e.g., Maniatis, Fritsch & Sambrook, *Molecular Cloning: A Laboratory Manual* (1982); *DNA Cloning*, Vols. I & II (D. N. Glover, ed. 1985); *Oligonucleotide Synthesis* (M. J. Gait, ed. 1984); *Transcription and Trans-*

*lation* (B. D. Hames & S. J. Higgins, eds. 1984); *Immobilized Cells and Enzymes* (IRL Press, 1986); B. Perbal, *A Practical Guide to Molecular Cloning* (1984).

In describing the present invention, the following terminology will be used in accordance with the definitions set out below.

"ADH II" refers to the glucose-repressible alcohol dehydrogenase II from yeast, particularly Saccharomyces, and in particular, *S. cerevisiae*. "ADH2" refers to the yeast gene encoding ADH II, as well as its associated regulatory sequences. See, e.g., Russell et al. (1983) J. Biol. Chem. 258:2674–2682.

"UAS" is an art-recognized term for upstream activation sequences or enhancer regions, which are usually short, repetitive DNA sequences located upstream from a promoter's TATA box. Of particular interest in the present invention is the ADH2 UAS, which is a 22-bp perfect inverted repeat located upstream from the ADH2 TATA box. See Shuster et al. (1986) Mol. Cell. Biol. 6:1894–1902.

"ADR1" refers to a positive regulatory gene from yeast required for the expression of ADH II. See, e.g., Denis et al. (1983) Mol. Cell. Biol. 3:360–370. The protein encoded by the ADR1 gene is referred to herein as "ADR I".

A "replicon" is any genetic element (e.g., plasmid, cosmid, chromosome, virus) that functions as an autonomous unit of DNA replication in vivo; i.e., capable of replication under its own control.

A "vector" is a replicon such as a plasmid, phage, or cosmid to which another DNA segment may be attached so as to bring about the replication of the attached segment.

A "double-stranded DNA molecule" refers to the polymeric form of deoxyribonucleotides (adenine, guanine, thymidine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of a particular double-stranded DNA molecule, sequences will be described herein according to the normal convention of giving only the sequence in the 5' to 3' direction along the nontranscribed strand of DNA, i.e., the strand having a sequence homologous to the mRNA produced from a particular coding sequence.

A DNA "coding sequence" is DNA sequence which can be transcribed and translated into a polypeptide in vivo when placed under the control of appropriate regulatory sequences. The boundaries of the coding sequence are determined by and include the translation start codon at the 5' (amino) terminus, and a translation stop codon at the 3' (carboxy) terminus. A coding sequence can include, but is not limited to, procaryotic DNA sequences, vital DNA sequences, cDNA or genomic DNA sequences from eucaryotic sources (e.g., mammalian), and even synthetic DNA sequences.

"Yeast-recognized transcription initiation and termination sequences" refer to DNA regulatory regions which flank a coding sequence and are responsible for the transcription in yeast of an mRNA homologous to the coding sequence which can then be translated into the polypeptide encoded by the coding sequence. Transcription initiation sequences include yeast promoter sequences, which are DNA regulatory sequences capable of binding yeast RNA polymerase in a cell and initiating transcription of a downstream (3' direction) coding sequence. For the purposes of defining the present invention, the promoter sequence is bounded at its 3' terminus by (and excludes) the translation start codon of a coding sequence and extends upstream (5' direction) to include the minimum number of nucleotides or elements necessary to initiate transcription at levels detectable above background. Within the promoter sequence will be found a transcription initiation site (conveniently defined by mapping with nuclease S1), as well as protein-binding domains (consensus sequences) responsible for the binding of the yeast RNA polymerase (e.g., the TATA box). Transcription initiation sequences can also include other regulatory regions responsible for promoter regulation or enhancement, such as UAS.

Promoters useful in the present invention include the wild-type ADR1 promoter, as well as other yeast promoters. Particularly preferred are promoters involved with the enzymes in the glycolytic pathway, e.g., phosphoglucoisomerase, phosphofructokinase, phosphotrioseisomerase, phosphoglucomutase, enolase, pyruvic kinase, glyceraldehyde-3-phosphate dehydrogenase (GAPD), ADH I, ADH II, as well as hybrids of these promoters. A particularly preferred hybrid promoter is the hybrid formed from the 5' regulatory sequences of the ADH2 gene (including the UAS) and the GAPD promoter transcription initiation site and consensus sequences, referred to as a "ADH2/GAPD hybrid promoter." See, e.g., EPO Publication Nos. 120,551 & 164,556; and 196,056; see also commonly owned U.S. patent application Ser. No. 868,639, filed 29 May 1986 and Ser. No. 845,737, filed 28 Mar. 1986. In like manner, a transcription terminator sequence located 3' to the translation stop codon can be either the wild-type ADR1, ADH2 or GAPD transcription termination sequences, or another yeast-recognized termination sequence, such as those from the genes for other glycolytic enzymes.

A coding sequence is "under the control" of transcription initiation and termination sequences when RNA polymerase binds the transcription initiation sequence and transcribes the coding sequence into mRNA terminating at the transcription termination sequence, and the mRNA is then translated into the polypeptide encoded by the coding sequence (i.e., "expression").

A "expression cassette" is a DNA construct comprising a coding sequence under the control of transcription initiation and termination sequences. In the practice of the present invention, such constructs will involve yeast-recognized transcription initiation and termination sequences, and the expression cassettes will include, for example, a coding sequence for the ADR1 protein or non-yeast protein, or both. It is particularly preferred to flank the expression cassettes with restriction sites that will provide for the convenient cloning of the cassettes into an appropriate vector.

A cell is "transformed" by exogenous DNA when such exogenous DNA has been introduced into the cell. The progeny of such cells that maintain the exogenous DNA are also referred to herein as "transformed" cells. Exogenous DNA may or may not be integrated (covalently linked) to chromosomal DNA making up the genome of the cell. The exogenous DNA may be maintained extrachromosomally in the transformed cell on a replicon such as a plasmid. When the exogenous DNA has become integrated into the chromosome, it is inherited by daughter cells through chromosome replication. A cell which has been transformed by exogenous DNA which is integrated into the chromosome is referred to as a "stably" transformed cell.

A "clone" or "clonal population" is a population of cells derived from a single cell or common ancestor by mitosis.

Two DNA sequences are "substantially homologous" when at least about 60% (preferably at least about 75%, and most preferably at least about 90%) of the nucleotides match over a defined length (e.g., 100 bp, 200 bp, 500 bp, 1 kb, 2 kb or more) of the molecules. Sequences that are substantially homologous can be identified in a Southern hybridization experiment under conditions of a selected stringency as defined for that particular system. Defining appropriate hybridization conditions is within the skill of the art. See, e.g., Maniatis et al., supra; *DNA Cloning*, supra; *Nucleic Acid Hybridization*, supra.

A "heterologous" region of a DNA molecule is an identifiable segment of DNA within a larger DNA molecule that is not found in association with the larger molecule in nature. An identifiable segment is a sequence of sufficient length to identify the sequence as having a source exogenous to the larger molecule or its source organism. Thus, when the heterologous region encodes a mammalian protein, the heterologous region will usually be flanked by DNA that does not flank the mammalian DNA sequence in the genome of the source organism. Another example of a heterologous coding sequence is a construct where the coding sequence itself is not found in nature (e.g., a cDNA where the genomic coding sequence contains introns, or synthetic sequences having codons different from organisms which encode the same or similar protein). Allelic variations, point mutations, or naturally occurring mutational events do not give rise to a "heterologous" region of DNA as used herein. A protein "heterologous" to an organism is a protein that is not encoded the organism's genome in nature. A "non-yeast" protein is heterologous to the yeast in question.

As used herein, "yeast" includes ascosporogenous yeasts (Endomycetales), basidiosporogenous yeasts and yeast belonging to the *Fungi imperfecti* (Blastomycetes). The ascosporogenous yeasts are divided into two families, Spermophthoraceae and Saccharomycetaceae. The latter is comprised of four subfamilies, Schizosaccharomycoideae (e.g., genus Schizosaccharomyces), Nadsonioideae, Lipomycoideae and Saccharomycoideae (e.g., genera Pichia, Kluyveromyces and Saccharomyces). The basidiosporogenous yeasts include the genera Leucosporidium, Rhodosporidium, Sporidiobolus, Filobasidium and Filobasidiella. Yeast belonging to the *Fungi Imperfecti* are divided into two families, Sporobolomycetaceae (e.g., genera Sporobolomyces, Bullera) and Cryptococcaceae (e.g., genus Candida). Of particular interest to the present invention are species within the genera Pichia, Kluyveromyces, Saccharomyces, Schizosaccharomyces and Candida. Of particular interest are the Saccharomyces species *S. cerevisiae, S. carlsbergensis, S. diastaticus, S. douglasii, S. kluyveri, S. norbensis* and *S. oviformis*. Species of particular interest in the genus Kluyveromyces include *K. lactis*. Since the classification of yeast may change in the future, for the purposes of this invention, yeast shall be defined as described in *Biology and Activities of Yeast* (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., *Biochemistry and Genetics of Yeast* (M. Bacila, B. L. Horecker & A. O. M. Stoppani eds. 1978); *The Yeasts* (A. H. Rose & J. S. Harrison eds., 2nd ed., 1987); *The Molecular Biology of the Yeast Saccharomyces* (Strathern et al. eds. 1981).

By way of example, the present invention will be described in relation to yeast of the genus Saccharomyces, particularly *S. cerevisiae*. The invention, however, is not limited to these yeasts.

The present invention, enhanced expression of heterologous protein in yeast, is achieved by placing the coding sequence for the heterologous protein under the control of ADH2 regulatory sequences within the yeast host, and also providing the yeast host with enhanced expression of ADR I. The construction of expression cassettes for non-yeast proteins employing ADH2 promoters, including hybrid ADH2 promoters such as the ADH2/GAPD hybrid promoter, is fully described in EPO Publication Nos. 120, 551 and 164,556.

The present invention employs yeast hosts having enhanced ADR I expression relative to wild-type yeast strains. When such yeast hosts are employed in conjunction with the above ADH2-based expression cassettes, there is a substantial increase in the production of heterologous protein produced from the ADH2 cassettes. Yeast hosts providing for the enhanced ADR I expression can be provided for in a number of ways.

In a preferred embodiment, enhanced ADR I expression is provided by transforming the yeast host with an expression cassette containing a coding sequence for ADR I (usually from the ADR1 gene), wherein the cassette provides for higher expression levels of ADR I in the host. The expression cassette can be comprised of the coding sequence under the control of ADR1 transcription initiation and termination sequences, or heterologous transcription initiation and termination sequences can be employed. In a preferred embodiment, the ADR I cassette is constructed using a strong yeast promoter in place of the ADR1 promoter; i.e., a promoter which provides for at least a 5-fold increase in transcription of a coding sequence relative to the ADR1 promoter. An example of such a promoter is the GAPD promoter.

The ADR I cassettes can be employed in transforming yeast hosts by either maintaining the cassette on an extra-chromosomal vector, such as a high copy number vector, or by integration into the yeast host genome via an integrating vector. The ADR I cassette and the non-yeast protein cassette can be maintained within the yeast host on either the same or different vectors, or can be incorporated into the host genome with the same or different integrating vector.

In a particularly preferred embodiment, the yeast host is transformed by an integrating vector carrying the ADR I cassette employing a strong yeast promoter, and the heterologous protein cassette is maintained on an extra-chromosomal, high copy vector. For example, the integrated ADR I cassette can use the GAPD promoter, and the extra-chromosomal non-yeast protein cassette can use the ADH2 promoter or the ADH2/GAPD hybrid promoter.

The replicons used in the present invention, usually plasmids, will include one or more replication systems, desirably two replication systems allowing for maintenance of the replicon in both a yeast host for expression and a bacterial (e.g., *E. coli*) host for cloning. Examples of such yeast-bacteria shuttle vectors include YEp24 [Botstein et al. (1979) Gene 8:17–24], pC1/1 [Brake et al. (1984) Proc. Natl. Acad. Sci. U.S.A. 81:4642–4646], and YRp17 [Stinchomb et al. (1982) J. Mol. Biol. 158:157]. Furthermore, an extra-chromosomal vector may be a high or low copy number vector, the copy number generally ranging from about 1 to about 500. With high copy number yeast vectors, there will generally be at least 10, preferably at least 20, and usually not exceeding about 150–500 copies in a single host. Depending upon the non-yeast protein selected, either a high or low copy number vector may be desirable, depending upon the effect of the vector and the foreign protein on the host. See, e.g., Brake et al., supra. DNA constructs of present invention can also be integrated into the yeast genome by an integrating vector. Examples of such vectors are known in the art. See, e.g., Botstein et al., supra.

a BglII restriction site. The sequence of the oligonucleotide adapter, which was prepared using yeast preferred codons instead of the codons normally present in the ADR1 gene, is as shown below.

```
                                              MetAlaAsnValGluLysProAsnAspCysSerGlyPheProValVal
              GATCTATTACCATGGCTAACGTTGAAAAGCCAAACGATTGTTCTGGTTTTCCAGTTGTT
                   ATAATGGTACCGATTGCAACTTTTCGGTTTGCTAACAAGACCAAAAGGTCAACAA
```

Preferably, less than 50 copies of the cassette are integrated into the genome, more preferably less than about 10, about 10, and usually less than about 5 (in addition any wild-type gene). Typically, only 1 or 2 copies are integrated.

The selection of suitable yeast and other microorganism hosts (e.g., diploid, haploid, auxotrophs, etc.) for the practice of the present invention is within the skill of the art. When selecting yeast hosts for expression, suitable hosts may include those shown to have, inter alia, good secretion capacity, low proteolytic activity, and overall robustness. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md.

Methods of introducing exogenous DNA into yeast hosts are well known in the art. There is a wide variety of ways to transform yeast. For example, spheroplast transformation is taught, for example, by Hinnen et al. (1978) Proc. Natl. Acad. Sci. U.S.A. 75:1919–1933, and Stinchcomb et al., EPO Publication No. 45,573. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The non-yeast protein can be harvested by any conventional means, and purified by chromatography, electrophoresis, dialysis, solvent-solvent extraction, and the like.

Examples

The following examples are provided for illustrative purposes only, and are not intended to limit the scope of the present invention. It is believed that the deposit of the starting biological materials is not necessary for the practice of the present invention since either the same or equivalent materials are publicly available. The disclosures of all of the references cited in the specification are presumed to be familiar to those of ordinary skill in the art, and are expressly incorporated herein by reference.

I.

Figure 2:
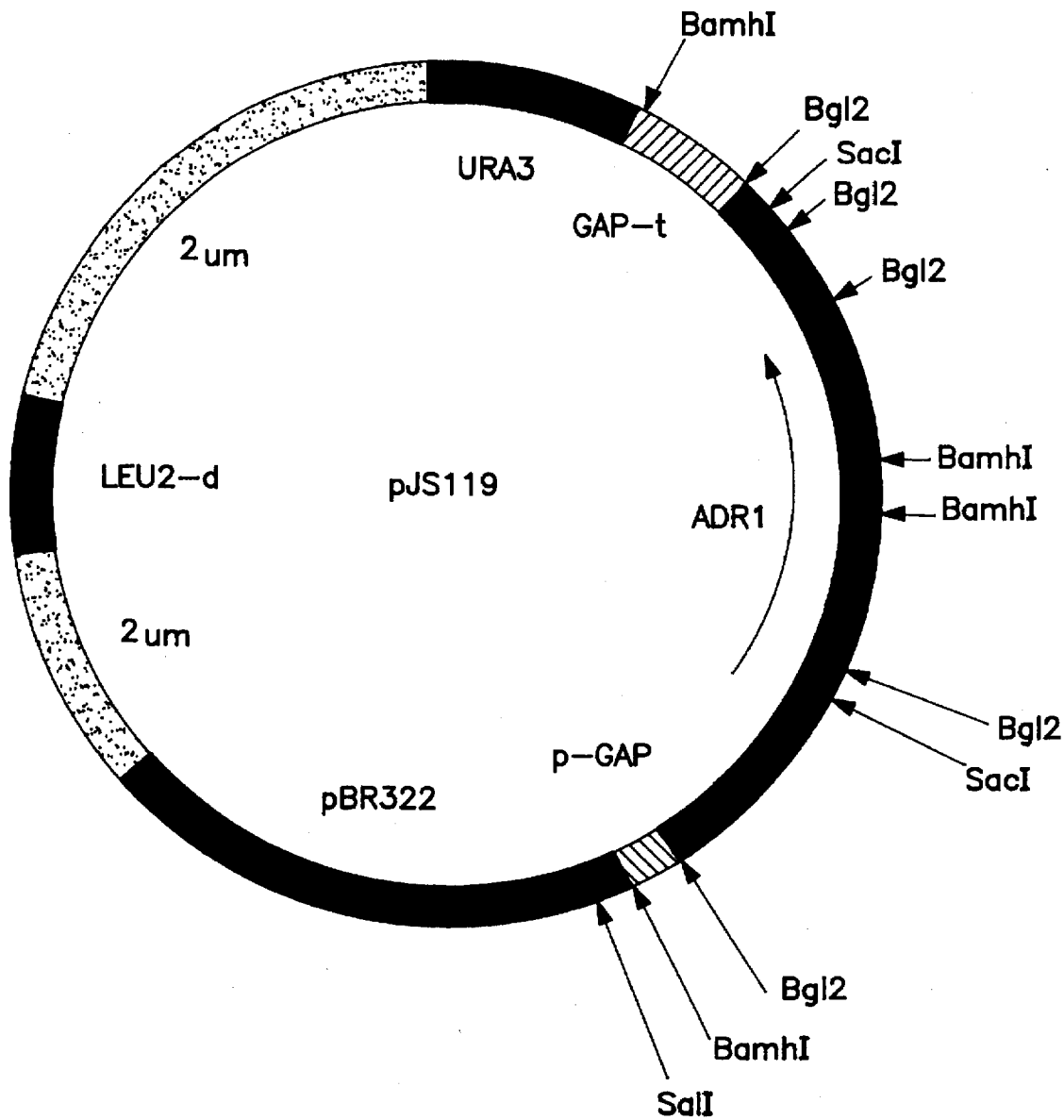
FIG. 2 is a restriction map of plasmid pJS119. Not all restriction sites are shown. The following abbreviations are used in the figure: URA3, yeast URA3 gene; LEU2-d, yeast LEU2-d gene; GAP-t, glyceraldehyde-3-phosphate dehydrogenase mRNA termination sequences; ADR1, yeast ADR1 gene; p-GAP, glyceraldehyde-3-phosphate dehydrogenase mRNA promoter start sequences; pBR322, E. coli plasmid sequences; 2 um, yeast 2 micron plasmid sequences.

This example describes the construction of an expression cassette for the enhanced expression of ADR I, its insertion into an autonomously replicating yeast vector, and the transformation of yeast strains therewith. FIG. 1 shows a flow diagram of the vector's construction, and FIG. 2 shows a partial restriction map of the resulting vector.

Plasmid YPp7-ADR1-411 [Denis et al. (1983) Mol. Cell. Biol. 3:360–370] contains the yeast ADR1 gene. This plasmid was cut with restriction enzyme HincII and a fragment isolated containing the ADR1 gene missing the codons for the first sixteen amino acids at the 5' end. An oligonucleotide was synthesized by standard methods to replace the N-terminal codons and to provide a 5'-extension containing The adapter was ligated to the HincII fragment from YPp7-ADR1-411 under standard conditions. After inactivating the ligase, the mixture was cut with BglII to create a 1.9 kb BglII fragment containing coding sequences for the first 641 amino acids of ADR I. This BglII fragment was then purified, recloned, and ligated into a BglII site between a GAPD promoter and a GAPD terminator in plasmid pAB27, such that the promoter would direct correct transcription of the ADR I coding sequence. The resulting plasmid was named pJS118.

Plasmid pAB27 is a yeast shuttle expression vector comprised of sequences from the yeast 2 micron plasmid, the *E. coli* pBR322 plasmid, the yeast marker genes URA3 and LEU-2d, and an "empty" GAPD expression cassette with a BglII insertion site disposed between the GAPD promoter and GAPD terminator sequences.

Plasmid pJS118 is an intermediate, since it codes for only the first 641 amino acids of ADR I. The remainder of the coding sequence from the ADR1 gene was then added to this vector to obtain pJS119. First, YRp7-ADR1-411 was cut with SacI and a 4 kb fragment was isolated containing the remaining coding sequence from ADR1 and its 3' flanking sequences. This 4 kb fragment was then ligated into SacI cut and alkaline phosphate treated pJS118 to create plasmid pJS119. The integrity of the ADR1 coding sequence was tested by restriction enzyme analysis to assure that the fragment had been inserted in the correct orientation. Plasmid pJS119 was transformed into two different yeast host strains, AB110 and JC482, using standard procedures. See, e.g., Hinnen et al. (1978) Proc. Natl. Acad. Sci. U.S.A. 75:1929.

Yeast strain AB110 was obtained by crossing *S. cerevisiae* 2150-2-3 (available from Lee Hartwell, University of Washington), with *S. cerevisiae* AB103.1 transformant containing pCl/1 derivative. The diploids were sporulated and the tetrads dissected. Strains were maintained on leucine selective plates in order to insure maintenance of the plasmid, since the parents are auxotrophs. A series of colonies were screened for their genotype with respect to a number of markers (Mat α, ura3, leu2, pep4-3). Strain AB110 was obtained by curing the resulting hybrid strain of its resident plasmid by growth in the presence of leucine (i.e., absence of selective pressure), and then selection for leu⁻ colonies by replica plating. AB110 has the following genotype: Mat α, ura3-52, leu2-04, or both leu2-3 and leu2-112, pep4-3, his4-580, cir°. A sample of this strain containing a different heterologous plasmid was deposited with the ATCC on 9 May 1984 under Accession No. 20709. See EPO Pub. No. 164,556.

Strain JC482 was obtained from Dr. John Cannon at the University of Pennsylvania, Pa. The strain was cured of resident 2 micron plasmid.

The above strains exhibit enhanced ADH II activity, and are suitable for transformation with an expression cassette for heterologous protein under the control of an ADH2 regulatory sequence, particularly expression cassettes on an integrating vector. Alternatively, such expression cassettes could be inserted into any convenient restriction site in pJS119, and the resulting vector used to transform an appropriate yeast strain.

II.

Figure 3:
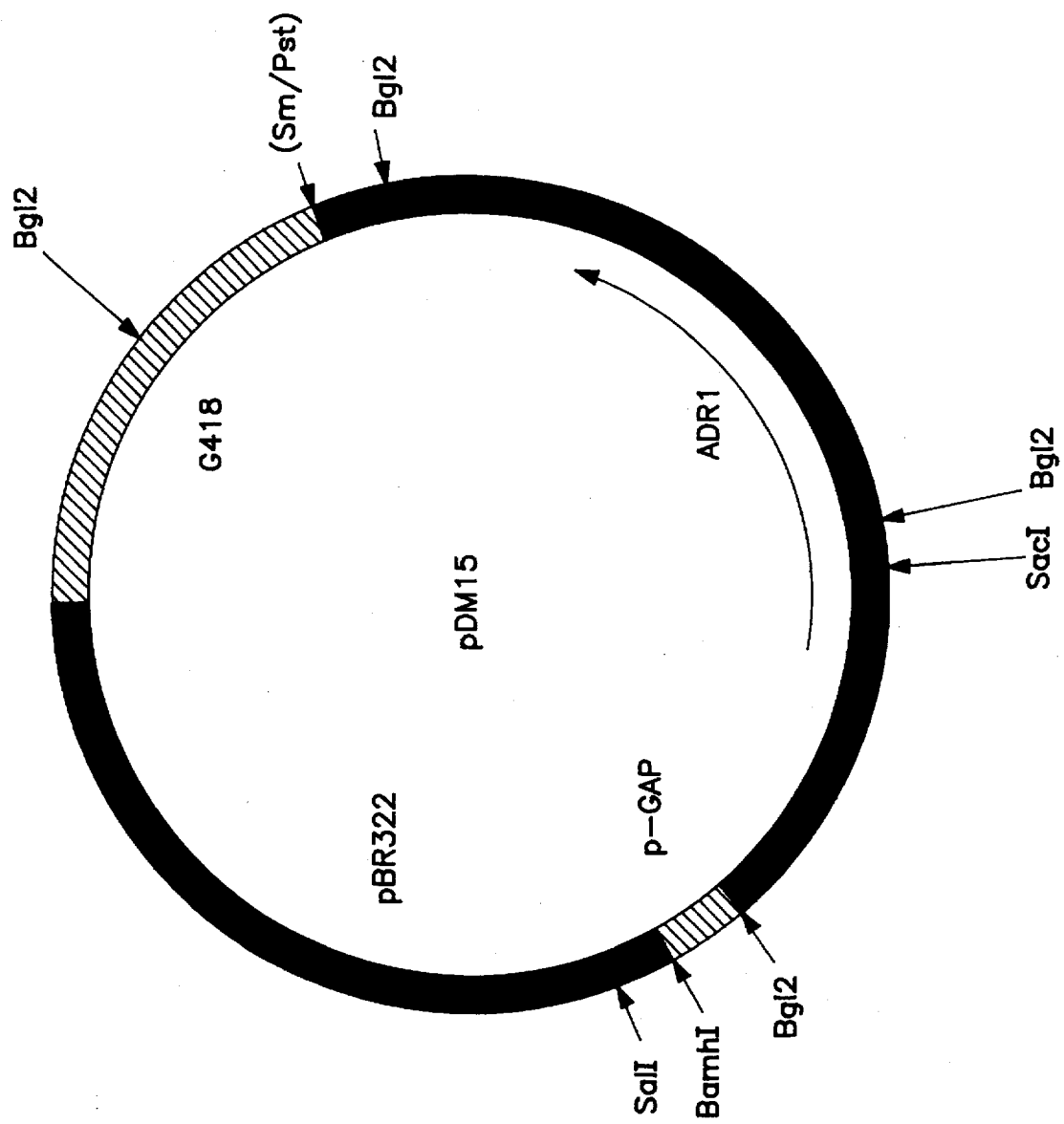
FIG. 3 is a restriction map of plasmid pDM15. Not all restriction sites are shown. The abbreviations are the same as for FIG. 2, with the following additions: G418, gene conferring resistance to G418 (Geneticin); (Sma/Pst), site of fusion between SmaI and PstI restriction sites.

This example describes the construction of an integrating vector containing an expression cassette for ADR I, and the transformation of yeast strains therewith. The integrating plasmid, pDM15, is shown in FIG. 3, and the construction is shown in the flow diagram in FIG. 1.

Plasmid pJS132 is a plasmid containing pBR322 sequences, and a gene coding for G418 resistance in yeast under the control of the Kluyveromyces lactis ADH1 promoter and terminator sequences. This plasmid is cut with SmaI and SalI, and the large linear fragment purified.

Plasmid pJS119 was cut with PstI, which cuts at a site downstream from the 3' end of the ADR I coding sequence. The cut plasmid was then treated with single-stranded specific S1 nuclease to create blunt ends, and then cut with SalI to provide a 6.2 kb fragment containing the ADR I expression cassette. Phenol extraction and ethanol precipitation were performed between each successive step. The SalI-blunt end fragment was then ligated to the large pJS132 fragment to create plasmid pDM15.

Plasmid pDM15 was then used to create ADR I overproducing saccaromyces strains by transforming yeast using standard procedures. For an example, strain AB110 was transformed to G418 resistance, and a strain exhibiting ADR I overproduction was isolated. This strain was designated JSC300. Another ADR I overproducer, JSC302, was made in a similar manner from strain BJ2168 (Yeast Genetic Center, supra) cured of its resident plasmid. Yet another ADR I overproducer is JSC308.

III.

The following example demonstrates the utility of yeast strains having enhanced production of ADR I as expression hosts for heterologous proteins.

Yeast strain JC300 was transformed by expression vectors for a superoxide dismutase (SOD)/insulin-like growth factor II (IGF II) fusion protein and for basic human fibroblast growth factor (hFGF).

The SOD/IGF II expression vector, pYLUIGF2-14, is described in EPO Pub. No. 196,056 and commonly owned U.S. patent application Ser. No. 845,737, filed 28 Mar. 1986. It is also deposited under ATCC Accession No. 20745 (27 Feb. 1985).

The basic hFGF expression vector, pA/G-hFGF, was prepared as follows. First, a synthetic hFGF gene was prepared by standard methods and having the following sequence:

Plasmid pBS100 [EPO Pub. No. 181,150 & commonly owned U.S. patent application Ser. No. 138,894, filed 24 Dec. 1987], contains ADH2/GAPD hybrid promoter cassette. The synthetic hFGF sequence was gel purified and cloned into NcoI/SalI digested pBS100 to place the hFGF sequence in the cassette. The cassette was cut from the pBS100/FGF plasmid with BamHI, and then cloned to the BamHI site of yeast shuttle vector pAB24. See commonly owned U.S. patent application Ser. No. 139,682, filed 30 Dec. 1987. The resulting vector was named pA/G-hFGF.

The above expression cassettes contained a UAS from the ADH2 gene. The strains were grown after transformation, and the heterologous protein recovered by standard procedures. Isolated protein was analyzed by SDS polyacrylamide gel electrophoresis. The expression of the SOD/IGF II fusion and hFGF in strains AB110 (control) and JCS300, demonstrated that there was an increase in the yield of non-yeast protein when JCS300 was used as the host.

Additional examples of high yield expression include polypeptides from the human immunodeficiency virus (HIV) type 1. For example, a polypeptide corresponding to the carboxy terminal half of HIV gp120env can be expressed at high levels. Examples of suitable expression vectors can be found in U.S. patent application Ser. No. 138,894, filed 24 Dec.1987. A particularly preferred vector disclosed therein is pBS24/SOD-SF2env4.

Deposit of Biological Materials

Samples of the following strains and plasmids were deposited with the American Type Culture Collection (ATCC), 12301 Parklawn Drive, Rockville, Md., U.S.A., and will be maintained under the provisions of the Budapest Treaty. The accession numbers and dates of these deposits are listed below.

| Deposited Material | ATCC Accession No. | Deposit Date |
| --- | --- | --- |
| S. cerevisiae JSC300 | 20878 | 5 May 1988 |
| S. cerevisiae JSC308 | 20879 | 5 May 1988 |
| pDM15 DNA | 40453 | 5 May 1988 |
| pJS119 DNA | 40454 | 5 May 1988 |

These deposits are provided for the convenience of those skilled in the art. These deposits are neither an admission that such deposits are required to practice the present invention, nor that equivalent embodiments are not within the skill of the art in view of the present disclosure. The public availability of these deposits is not a grant of a license to make, use or sell the deposited materials under this or any other patent. The nucleic acid sequences of the deposited materials are incorporated in the present disclosure by reference and are controlling if in conflict with any sequences described herein.

Although the foregoing invention has been described in some detail by way of illustration and example for purposes of clarity and understanding, it will be obvious that changes and modifications may be practiced within the scope of the appended claims.

```
CATGGCCGCCGGGAGCATCACCACGCTGCCAGCCCTGCCGGAGGACGGGGGCAGCGGCGC
CTTCCCCCCAGGCCATTTCAAGGACCCAAAGAGACTGTACTGTAAGAACGGCGGGTTCTT
CCTGAGAATCCATCCCGACGGCAGGGTCGATGGCGTGAGAGAGAAGAGCGACCCTCATAT
CAAGCTTCAGCTGCAGGCCGAGGAGAGGGGCGTGGTCTCCATCAAGGGCGTCTGTGCCAA
CAGGTACCTGGCCATGAAGGAGGACGGCAGGCTGCTGGCCTCCAAGTGTGTCACCGACGA
GTGTTTCTTCTTCGAGAGGCTGGAGTCCAACAACTACAACACCTACCGGTCAAGGAAATA
CACCAGCTGGTACGTCGCCCTGAAGAGGACCGGCCAGTACAAGCTGGGATCCAAAACAGG
ACCTGGGCAGAAGGCCATCCTGTTCCTGCCCATGTCCGCCAAGTCCTAATAGTCGAC
```

I claim:

1. A method of expressing a non-yeast protein in a yeast host comprising:

(A) providing a yeast host that comprises:
  (i) a first expression cassette comprising (a) a first DNA coding sequence that encodes a non-yeast protein, (b) a first yeast-recognized transcription initiation sequence, and (c) a first yeast-recognized termination sequence,
    wherein the first DNA coding sequence is under the control of the first transcription initiation sequence and the first termination sequence, and
    wherein the first transcription initiation sequence comprises a yeast ADH2 upstream activation site and a first yeast promoter heterologous to the ADH2 upstream activation site;
  (ii) a second expression cassette heterologous to the yeast host comprising (a) a second DNA coding sequence that encodes ADR I; (b) a second yeast-recognized transcription initiation sequence, and (c) a second yeast-recognized termination sequence,
    wherein the second DNA coding sequence is under the control of the second transcription initiation sequence and the second termination sequence, and
    wherein the second transcription initiation sequence comprises a second yeast promoter,
(B) culturing a clonal population of the yeast host under condition whereby the non-yeast protein and ADR I are expressed; and
(c) recovering the non-yeast protein from the clonal population.

2. The method of claim 1, wherein said first promoter is an ADH2/GAPD hybrid promoter.

3. The method of claim 1, wherein said second yeast-recognized transcription initiation sequence comprises non-ADRI promoter.

4. The method of claim 3, wherein said second yeast-recognized transcription initiation sequence comprises the GAPD promoter.

5. The method of claim 1, wherein said second expression cassette is maintained on an extra-chromosomal vector.

6. The method of claim 5, wherein said vector is a high copy number plasmid.

7. The method of claim 1, wherein said second expression cassette is integrated into the genome of said yeast host.

8. The method of claim 4, wherein said second expression cassette is integrated into the genome of said yeast host.

9. The method of claim 8, wherein said first promoter is a hybrid ADH2/GAPD promoter.

10. A transformed yeast host comprising:
  (i) a first expression cassette comprising (a) a first DNA coding sequence that encodes a non-yeast protein, (b) a first yeast-recognized transcription initiation sequence, and (c) a first yeast-recognized termination sequence,
    wherein the first DNA coding sequence is under the control of the first transcription initiation sequence and the first termination sequence, and
    wherein the first transcription initiation sequence comprises a yeast ADH2 upstream activation site and a first yeast promoter heterologous to the ADH2 upstream activation site;
  (ii) a second expression cassette heterologous to the yeast host comprising (a) a second DNA coding sequence that encodes ADR I; (b) a second yeast-recognized transcription initiation sequence, and (c) a second yeast-recognized termination sequence,
    wherein the second DNA coding sequence is under the control of the second transcription initiation sequence and the second termination sequence, and
    wherein the second transcription initiation sequence comprises a second yeast promoter.

11. The yeast of claim 10, wherein said first promoter is an ADH2/GAPD hybrid promoter.

12. The yeast of claim 10, wherein said first expression cassette is maintained in said yeast on an extrachromosomal vector.

13. The yeast of claim 11, wherein said first expression cassette is maintained in said yeast on an extrachromosomal vector.

14. The yeast of claim 11, wherein said wherein said second expression cassette is integrated into the genome of said yeast.

15. The yeast of claim 12, wherein said wherein said second expression cassette is integrated into the genome of said yeast.

16. The yeast of claim 14, wherein said second promoter is a GAPD promoter.

17. The yeast of claim 15, wherein said second promoter is a GAPD promoter.

18. A transformed yeast comprising an expression cassette integrated into the genome containing a coding sequence for ADRI under the control of yeast-recognized transcription initiation and termination sequences, said transcription initiation sequence being other than the ADRI promoter.

19. The yeast of claim 18, wherein said transcription inititation sequence is a strong yeast promoter.

20. The yeast of claim 19, wherein said strong yeast promoter is a yeast glycolytic enzyme promoter.

21. The yeast of claim 19, wherein said strong yeast promoter is the GAPD promoter.

* * * * *